(12) United States Patent
Gebrian et al.

(10) Patent No.: US 7,661,551 B2
(45) Date of Patent: Feb. 16, 2010

(54) MULTI-COMPARTMENT REAGENT CONTAINER HAVING MEANS TO INHIBIT RE-USE THEREOF

(75) Inventors: Peter Louis Gebrian, Wilmington, DE (US); William Jackson Devlin, Sr., New London, PA (US); Timothy Patrick Evers, Wilmington, DE (US); Thai Huynh-Ba, Newark, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 591 days.

(21) Appl. No.: 10/858,156

(22) Filed: Jun. 1, 2004

(65) Prior Publication Data
US 2004/0217031 A1 Nov. 4, 2004

Related U.S. Application Data

(62) Division of application No. 09/949,132, filed on Sep. 7, 2001, now Pat. No. 6,943,030.

(51) Int. Cl.
*B65D 25/04* (2006.01)
(52) U.S. Cl. ............... 220/507; 220/500
(58) Field of Classification Search ......... 220/4.26, 220/4.27, 475, 481, 23.8, 23.2, 23.83, 500, 220/555, 646, 660, 669, 694, 729, 890
See application file for complete search history.

(56) References Cited

U.S. PATENT DOCUMENTS

| | | | |
|---|---|---|---|
| 3,875,620 A * | 4/1975 | Wells et al. ............... 24/16 PB |
| 3,925,139 A | 12/1975 | Simmons |
| 4,286,640 A | 9/1981 | Knox et al. |
| 4,306,448 A | 12/1981 | Rhode |
| 4,390,499 A | 6/1983 | Curtis et al. |
| 4,591,062 A | 5/1986 | Sandhaus |
| 4,724,972 A | 2/1988 | Marcus |
| 5,008,082 A | 4/1991 | Shaw |
| 5,009,942 A * | 4/1991 | Benin et al. ............... 428/36.6 |
| 5,075,082 A * | 12/1991 | Fechtner ................. 422/102 |
| 5,133,470 A | 7/1992 | Abrams et al. |
| 5,255,804 A | 10/1993 | Butterbrodt |
| 5,322,668 A | 6/1994 | Tomasso et al. |
| 5,403,551 A | 4/1995 | Galloway et al. |
| 5,472,415 A | 12/1995 | King et al. |
| 5,518,693 A | 5/1996 | Tomasso et al. |
| 5,578,272 A | 11/1996 | Koch et al. |
| 5,645,824 A | 7/1997 | Lim et al. |
| 5,690,246 A | 11/1997 | Anderson et al. |
| 5,885,529 A | 3/1999 | Babson et al. |
| 5,968,453 A * | 10/1999 | Shugart ................. 422/102 |
| 5,976,469 A | 11/1999 | Davis |
| 6,043,097 A | 3/2000 | Dumitescu et al. |
| 6,149,872 A | 11/2000 | Mack et al. |
| 6,405,481 B1 * | 6/2002 | Bautner ................. 47/77 |

* cited by examiner

*Primary Examiner*—Stephen Castellano
(74) *Attorney, Agent, or Firm*—Leland K. Jordan

(57) ABSTRACT

A method for automatically determining whether a reagent container is new and unused or whether the reagent container has been previously used whenever reagent containers are initially placed onto an analyzer. Unused containers have a flag or lock-out member that can be dislodged or relocated by a moveable sensor probe when containers are placed onto the analyzer.

22 Claims, 10 Drawing Sheets

MULTI-COMPARTMENT REAGENT CONTAINER HAVING MEANS TO INHIBIT RE-USE THEREOF

This application is a divisional of application Ser. No. 09/949,132 filed Sep. 7, 2001, now U.S. Pat. No. 6,943,030.

FIELD OF THE INVENTION

The present invention relates to a method and apparatus for automatically processing a patient's biological fluids such as urine, blood serum, plasma, cerebrospinal fluid and the like. In particular, the present invention provides a method to prevent accidental re-use of reagents contained within a previously used reagent container.

BACKGROUND OF THE INVENTION

Various types of tests related to patient diagnosis and therapy can be performed by analysis for an analyte within a sample of a patient's infections, bodily fluids or abscesses. Patient samples are combined with various assay reagents in reaction vessels; the mixture is then incubated and analyzed using interrogating radiation measurements to aid in treatment of the patient. Automated clinical analyzers for chemical, immunochemical and biological testing of such sample-reagent mixtures are well known, typically adding one or two assay reagents to a liquid sample, the reagents being obtained from reagent storage compartments maintained on-board the analyzer.

For convenience and compactness within an automated chemical analyzer, it is desirable to store all reagents needed to conduct a single assay within contiguous compartments or vessels. Typical of such vessels is the multi-compartment reagent container available for use in an analyzer known as the Dimension® Chemical Analyzer, sold by Dade Behring Inc., Deerfield, Ill. This multi-compartmented container is in the form of a container strip described in U.S. Pat. No. 4,720,374, entitled "Container Having a Sonication Compartment", issued to Ramachandran, and includes a rigid peripheral band formed of an inert plastic. The band is formed integrally with each of several reagent containers so that the container strip generally tapers in a substantially elongated wedge-like manner from a first edge to a second edge. The wedge-shaped plan profile for the container strip facilitates the mounting of a plurality of such strips in a circumferentially adjacent generally radially extending relationship across a rotatable reagent carrying plate, like described in U.S. Pat. No. 4,863,693, entitled "Analysis Instrument Having A Blow Molded Reaction Chamber", issued to Howell, and having a reagent supply arrangement with an array of multi-compartment reagent containers disposed in substantially radial directions from the vertical center of rotation of rotatable plate. The reagent containers may be refrigerated or cooled, if desired, as is discussed therein. The reagent supply includes a reagent dispensing probe that is movable in substantially radially inward or radially outward directions with respect to the plate to aspirate a selected reagent from any one of the segmented reagent compartments of the multi-compartment reagent containers and to deposit a predetermined amount of reagent into one or more of a number of reaction vessels disposed at angular positions arranged around the periphery of the plate.

The tops of the multi-compartment reagent containers may be sealed with a suitable laminate that prevents gas and vapor escape and yet permits penetration by a probe for aspiration etc. The plastic used for the receptacle is polyethylene and the laminate is a three-ply laminate of a polyester film, a polyvinylidene chloride coating on the polyester film, and finally a sheet of polyethylene adhered to the coating. The laminate is heat sealed to the peripheral surface of the polyethylene compartments with the lower polyethylene sheet contacting the compartment rim. Variations of such a multi-compartment reagent container are described in U.S. Pat. Nos. 4,935,274 and 5,009,942 all of which are assigned to the assignee of the present invention.

A persistent problem with the use of reagent containers as employed on automated clinical analyzers is accidental attempts to re-use reagent containers that have been previously used on such an analyzer. When a container is used on an analyzer, partial amounts of reagents are removed by reagent aspiration devices; if the container is removed from the analyzer, it is possible that reagent quantities remaining therein may become contaminated or stored in a hostile environment so that their reactive characteristics become altered. In such instances, erroneous analytical results may be reported by the analyzer before the situation is noted and corrected. Accordingly, it is desirable whenever a reagent container is initially placed onto an analyzer, that an automated method be provided to determine whether the container is new and unused or whether the reagent container has been previously used.

U.S. Pat. No. 5,976,469 discloses an analytical specimen cup having a removable lid of a type for defining a test space with a chemical strip mounted therein; the cup includes a selectively-removable protective cover for selectively covering and uncovering an outer surface of a transparent portion of an outer partition forming the test space. The protective cover is formed as one piece with an inner partition to be attached thereto by a dual living hinge. The lid is rectangular in shape and includes an elongated magnifying lens which has protrusions extending into blind holes of the inner partition. The magnifying lens extends across the transparent portion of the outer partition. When the protective cover is in a closed position it impinges on the magnifying lens.

U.S. Pat. No. 5,645,824 discloses a color changing reagent composition for coating onto syringe needles and other needle containing medical devices which upon contact with such bodily fluids as blood, mucous, saliva, and semen will cause the composition coated needle to change in color to signal a prior use and contamination with a possibly infected bodily fluid.

U.S. Pat. No. 5,472,415 discloses an instrument for evaluating the fit of a corresponding orthopedic implant. The instrument is intended and designed to be a disposable, single use provisional instrument component. The provisional instrument component is made of a material which can be sterilized by gamma irradiation, but which provides a visible indicator, such as visible deformation, upon re-sterilization by exposure to a heated environment, thereby discouraging or preventing re-use of the component.

U.S. Pat. No. 5,403,551 discloses an assaying device for both collecting and analyzing a sample which includes a container and an opening for collecting the sample in a chamber for storing the sample. A cap is provided for sealing the container opening and at least one assay system is attached to the container for chemically analyzing the sample. A channel is provided for enabling a portion of the sample to enter the assay system upon a change of orientation of the container. A tamper-proof device is provided through the use of a releasable seal which permits the sample to enter the assay system only when desired.

U.S. Pat. No. 5,255,804 discloses a tamper-proof closure for a tube includes a neck projection on a neck of the tube, which neck projection is riveted to an edge of a sleeve section provided in a cap. After the neck projection has been broken off to use the tube, the cap can be replaced on the tube, however, the connection is so loose that when the tube is picked up again, the cap is immediately detached from the neck, thus indicating prior use.

U.S. Pat. No. 4,591,062 discloses a tamper-evident closure apparatus for internally pressurized containers includes a closure provided with a mechanism for venting the internal pressurized gas upon initial unsealing of the container and a tamper-indicating device adapted to be acted upon by the vented gas to indicate that an initial unsealing of the container has occurred. The tamper-indicating device may be, for example, chemically activated to change colors when acted upon by the vented gas or may be mechanically activated so that venting of the pressurized gas causes a visibly apparent disruption, distortion or the like to indicate initial unsealing of the container.

U.S. Pat. No. 4,286,640 discloses a tamper-resistant cover for the port of a container for medical liquids which when applied to the port indicates that an additive material has been introduced into the container. The port cover is molded from a resinous plastic material and includes latch portions which fit into a latch bar with the latch bar serving as a means to prevent access with the latch portions so as to result in a tamper-resistant structure. The latch portions are in the form of barbed sections and are guided by means of an inclined ramp into latch openings in such a manner that a compression fit is provided so that after the barbed sections are forced through the latch openings the barbed sections will expand to engage latch surfaces in the latching bar.

From this discussion of the state of art in automated clinical analyzers, it may be seen that while there has been progress toward introduction of tamper-evident containers, there has been no progress made toward reducing the potential problems caused by re-use of a clinical assay reagent container. Thus, there remains an unmet need for a method and reagent container adapted to disable an analyzer whenever a previously used reagent container is presented to the analyzer, and/or to alert an operator that results reported by the analyzer were obtained using a previously used reagent container and that the assay results may therefore be suspect.

SUMMARY OF THE INVENTION

The principal object of the invention is to provide a method for automatically determining whether a reagent container is new and unused or whether the reagent container has been previously used whenever a reagent container is initially placed onto an analyzer. In a first exemplary embodiment of the present invention, whenever a reagent container is placed onto a clinical analyzer, a moveable sensor probe within the analyzer determines the presence or absence of a lock-out member attached to the reagent container. Analysis of the length of travel of the probe, taken with the displacing force of the probe and the resilience of the lock-out member, is undertaken to ensure that the reagent container is new and unused. In addition, attempts to over-ride the lock-out member may be detected if the length of travel of the probe and the displacing force do not fall within previously predetermined ranges. In this embodiment, the lock-out member may be dislodged from the container by the probe.

In an alternate embodiment of the invention, the lock-out member is of a "two-position snap" design in which a selectively weakened bridge member is displaced or toggled from an original "new" location to a "used" location whenever the container is initially placed onto the analyzer. In this embodiment, the bridge member is retained as a permanent but displaced portion of the reagent container. In practicing either embodiment of the present invention, the analyzer may be programmed to automatically eject a previously used reagent container; alternately, the analyzer may allow sample analysis to continue uninterrupted with reagents from a previously used container but automatically noting such re-use in the reported analytical results.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
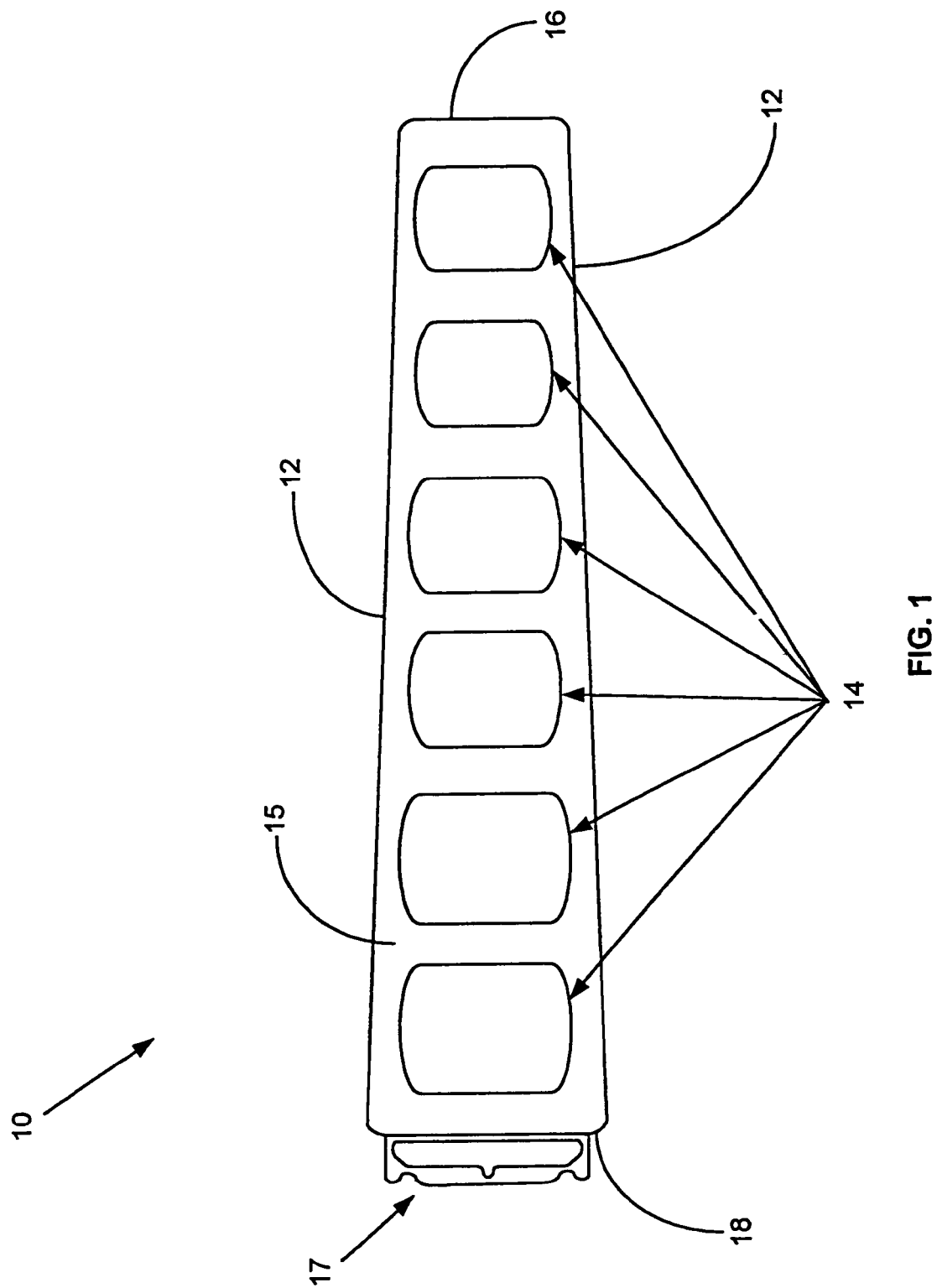
FIG. 1 is a schematic plan view of a reagent container having features needed to practice an exemplary embodiment of lock-out features of the present invention.
Figure 2:
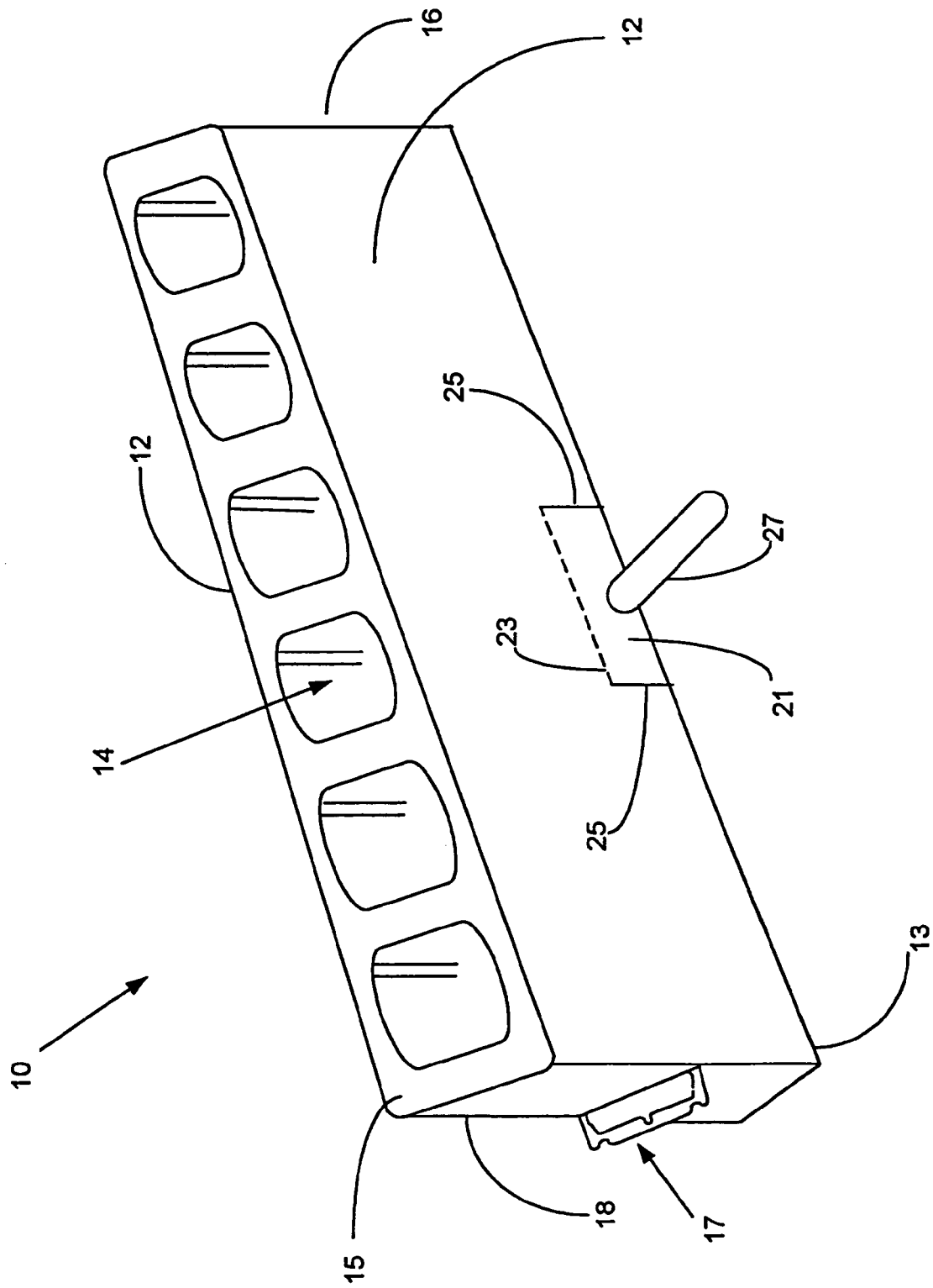
FIG. 2 is an isometric view of the reagent container of FIG. 1 illustrating an alternate lock-out embodiment of the present invention.

FIG. 1, taken with FIG. 2, shows schematically the elements of a multi-compartment reagent container 10 comprising a plurality of compartments 14 arranged in an end-to-end relationship to form a container strip generally enclosed between two sidewalls 12 depending downwardly from a top surface 15. The reagent container 10 may be fabricated in any convenient manner and formed of suitable material such as an inert plastic. The top surface 15 is joined to or is preferably formed integrally with each of the compartments 14 such that reagent container 10 generally tapers in a substantially elongated wedge-like manner from a first wider edgewall 18 to a second less wide edgewall 16. This wedge-shaped plan profile for the container 10 facilitates the mounting of a plurality of such reagent containers 10 in a circumferentially adjacent, generally radially extending relationship across a rotatable reagent carrying plate (U.S. Pat. No. 4,863,693). It should be appreciated however that the individual containers may take any predetermined configuration and may be used alone or arranged together in any convenient number and remain within the contemplation of this invention.

As is described in the aforementioned U.S. Pat. No. 4,720,374, such reagent containers 10 are sold under the tradename FLEX(™) cartridge by Dade Behring Inc, Deerfield, Ill., and contain reagents as necessary to perform a particular given assay. Each of the compartments 14 generally have the form of a closed well defined by generally opposed pairs of generally parallel and integrally formed sidewalls and endwalls. The upper surfaces of the sidewalls and the endwalls together with the upper surface 15 of the reagent container 10 in the vicinity thereof register to define a substantially planar sealing surface peripherally surrounding the open upper end of the compartments 14. Each of the compartments 14 is closed by a downwardly sloping floor. The top surface 15 of the multi-compartment reagent container 10 may be sealed with a suitable laminate (not shown) that prevents gas and vapor escape and yet permits penetration by a probe for aspiration, etc.

Figure 2A:
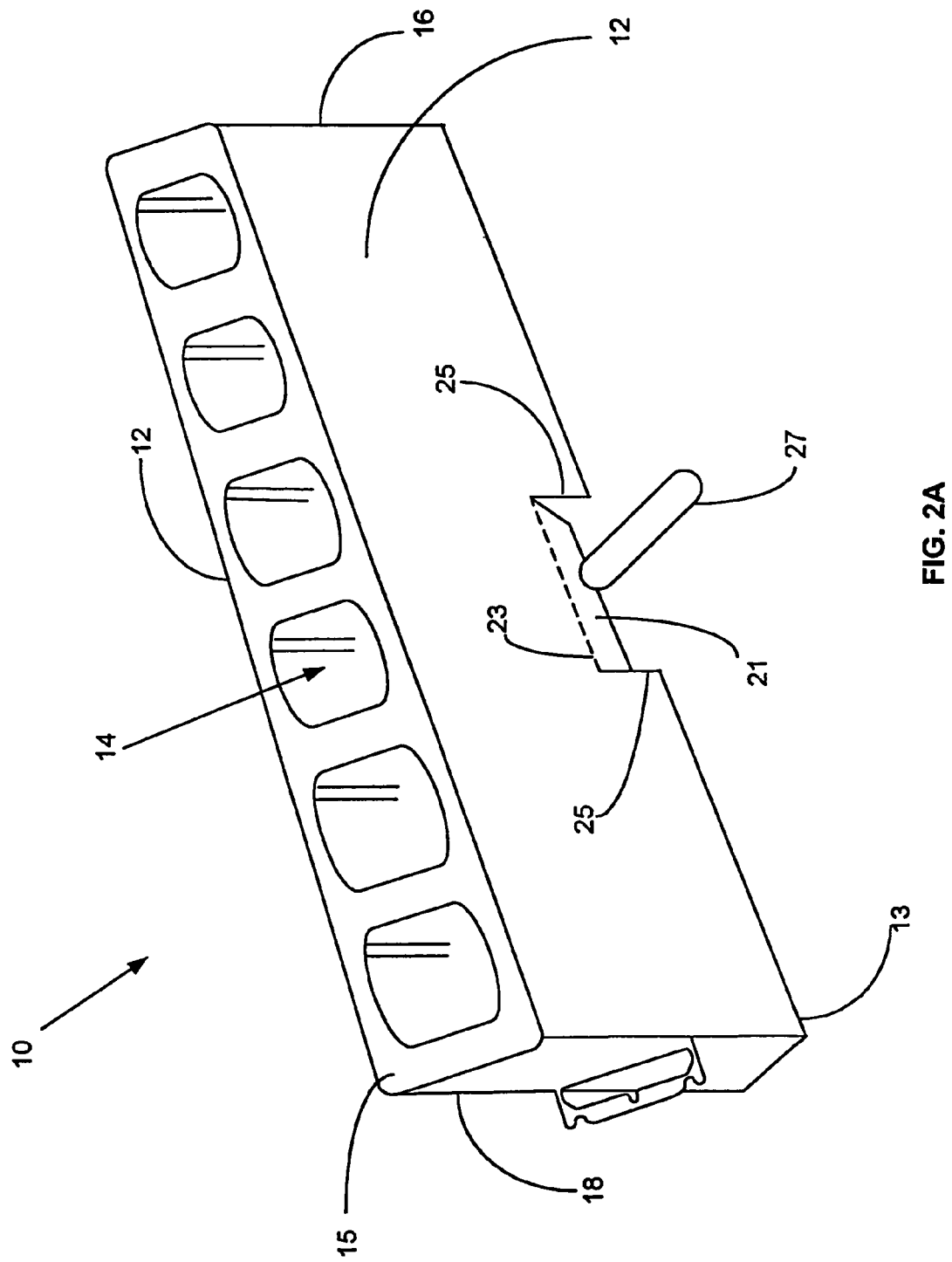
FIG. 2A is an isometric view of the alternate lock-out embodiment of FIG. 2 illustrating the use of a sensor probe in breaking away a flag portion of the reagent container of FIG. 1.

A principal object of the present invention is to provide a method for automatically determining whether the reagent container 10 is new and unused or whether the reagent container 10 has been previously used whenever reagent container 10 is initially placed onto an analyzer. The terms "new" and "unused" are meant to convey a condition of having not previously been placed into an analyzer, irregardless of whether or not reagents have been extracted from compartments 14. In a first embodiment of the present invention, reagent container 10 is provided with a punch-out flag member 21 (FIGS. 2 and 2A) having the shape of a rectangular tab in a lowermost portion of either sidewall 12. Flag member 21 is preferably formed when container 10 is molded and is of the same material as is container 10 but is attached to sidewall 12 only along a weakened top flag edge 23 (shown in dotted lines) and is unattached to sidewall 12 along two sidewall edges 25 of the flag member 21. Obvious equivalents to flag member 21 include sidewall, endwall, top or bottom flag-like portions having circular, oblong and similar shapes and which are semi-attached to container 10. When container 10 is placed onto the analyzer, a moveable sensor probe 27 inside the analyzer is automatically extended by an appropriate actuator into contact with flag member 21. Sensor probe 27 comprises a conventional pressure-reading sensor and displacement transducer adapted to provide electronic signals indicative of the resistive forces encountered by probe 27 as well as of the length of travel of sensor probe 27. Such probes are well known in the art, being supplied by companies like Schaevitz Engineering, Hampton Va. Upon contact with flag member 21, sensor probe 27 generates a non-zero resistive force signal like that shown by letter "C" corresponding to a position #1 in FIG. 3 where the probe 27 is initially brought into physical contact with container 10. Continued movement of sensor probe 27 inwardly into the body of container 10 corresponding to a position #2 in FIG. 3 causes a bending along weakened flag edge 23 of flag member 21 inwardly from sidewall 12, accompanied by increased resistive forces as indicated by the letter "B" in FIG. 3. Even further continued movement of sensor probe 27 inwardly into the body of container 10 causes weakened flag edge 23 to rupture and snap flag member 21 free from sidewall 12, as indicated by the letter "S" in FIG. 3 corresponding to a position #3. It is well within the skill of art to adjust the thrust forces of signal probe 27 in accord with the connective strength of weakened flag edge 23 to obtain such tensile and rupturing forces for relatively brittle materials of construction. Alternately, in an embodiment in which container 10 is constructed of less brittle and more pliable materials, flag member 21 may be bent inwardly and not dislodged from container 10. Such situations permit that the flag member 21 may be re-bent outwardly near its original location and the signals generated by probe 27 may not be as reliable as desired.

It is well within the state of art for the analyzer to be equipped with computer-implemented control programs that monitor the shape of the signal curve generated by sensor probe 27 to confirm from the length of travel of the probe 25, taken with the displacing force of the probe 27 and the resilience of the flag member 21, that reagent container 10 is new and unused. In particular, if no resistive forces are indicated by probe 27 in moving between probe positions #1 and #2, it may be concluded that container 10 has been previously "used" since flag member 21 has been previously displaced from its original location in a plane coincident with sidewall 12 of the container. In such an instance, container 10 is not being presented to the analyzer in a "new, unused" condition and no guarantee may be presumed for the quality of the reagents contained therein. A key feature of the present invention is that whenever a container 10 is initially placed onto an analyzer, if the length of travel of probe 27 and the displacing force do not fall within previously predetermined ranges, for example within a range indicated by a dashed lines R of about 15% to 20% of the relative values indicated in FIG. 3, it may be automatically determined that a reagent container has been previously used. In such an instance, the analyzer may optionally be caused to eject the previously used container, to enter a stand-by condition and signal for operator attention, or to complete the requested test assays and provide a warning signal concerning the quality of assay results. Conversely, if the length of travel of probe 27 and the displacing force do fall within previously predetermined ranges, for example within a range indicated by a dashed lines R of about 15% to 20% of the relative values indicated in FIG. 3, it may be automatically determined that a reagent container has not previously used. In such an instance, the analyzer may optionally be caused to complete the requested test assays and provide a signal or report that the assays were completed with reagents from a new container 10.

In this first embodiment, flag member 21 is typically dislodged from container 10 by sensor probe 27 and may therefore interfere with automated operation of the analyzer. Flag member 21 may be constructed of materials like paper, thin plastic, or cloth and attached to container 10 at all boundaries and may be easily penetrated by moveable sensor probe 27. In such embodiments, flag member 21 would be caused to stretch inwardly by sensor probe 27 before rupturing. Signals similar to those illustrated in FIG. 3 would still be obtained.

Figure 4:
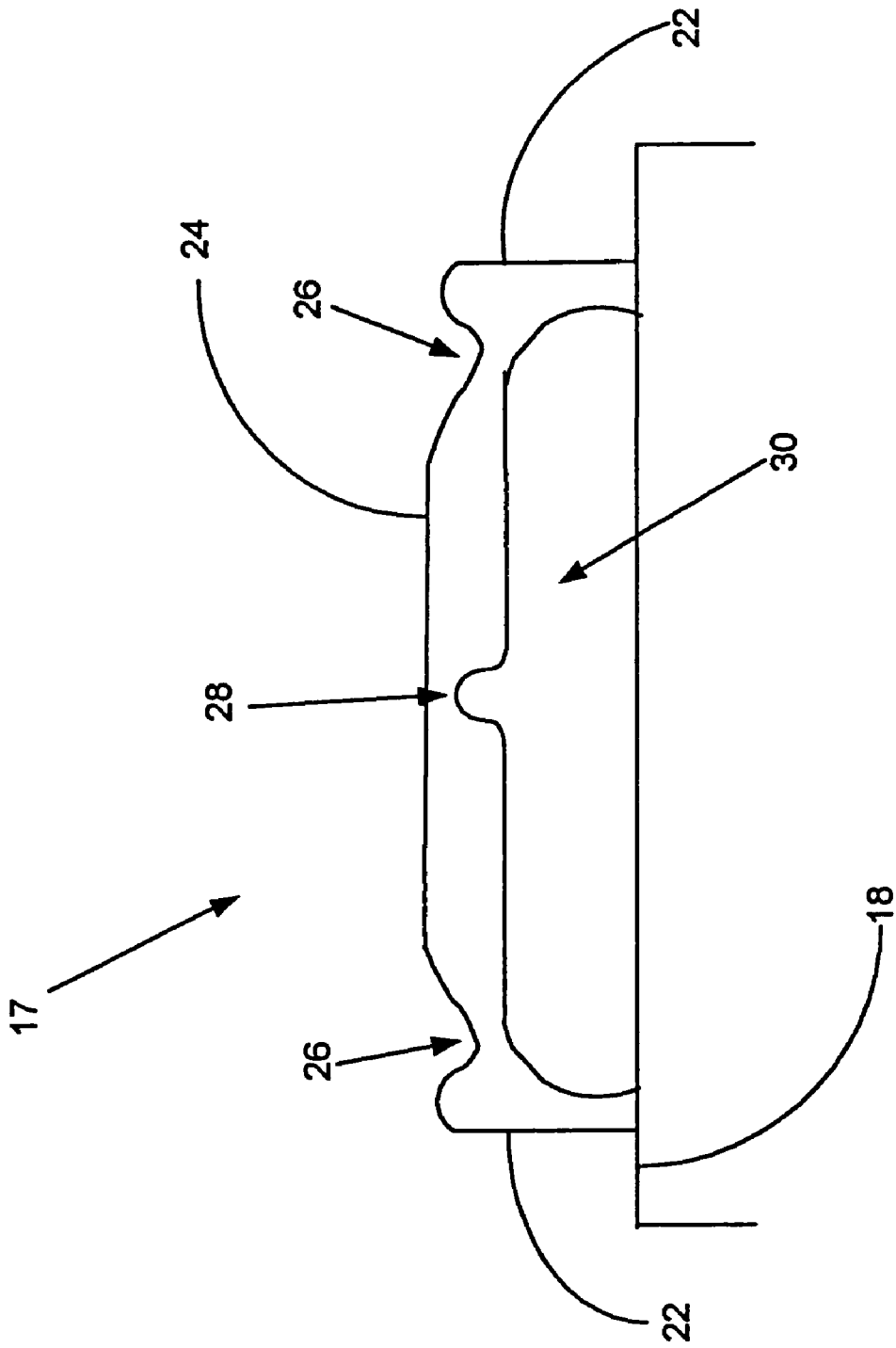
FIG. 4 is an enlarged view of an exemplary lock-out member of the reagent container of FIG. 1 in an unused condition.
Figure 5:
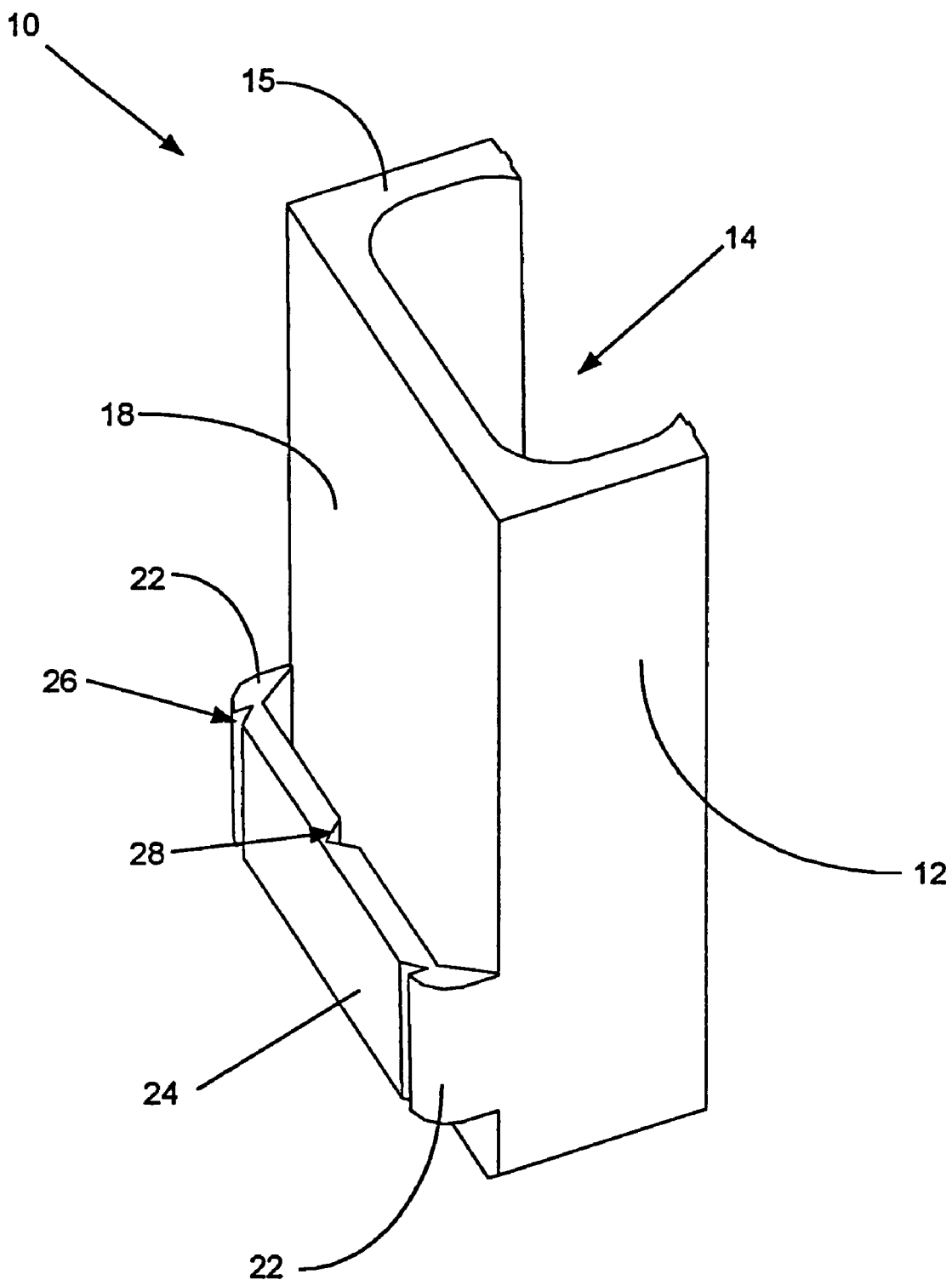
FIG. 5 is an isometric view of the lock-out member of FIG. 4 in an unused condition.
Figure 6:
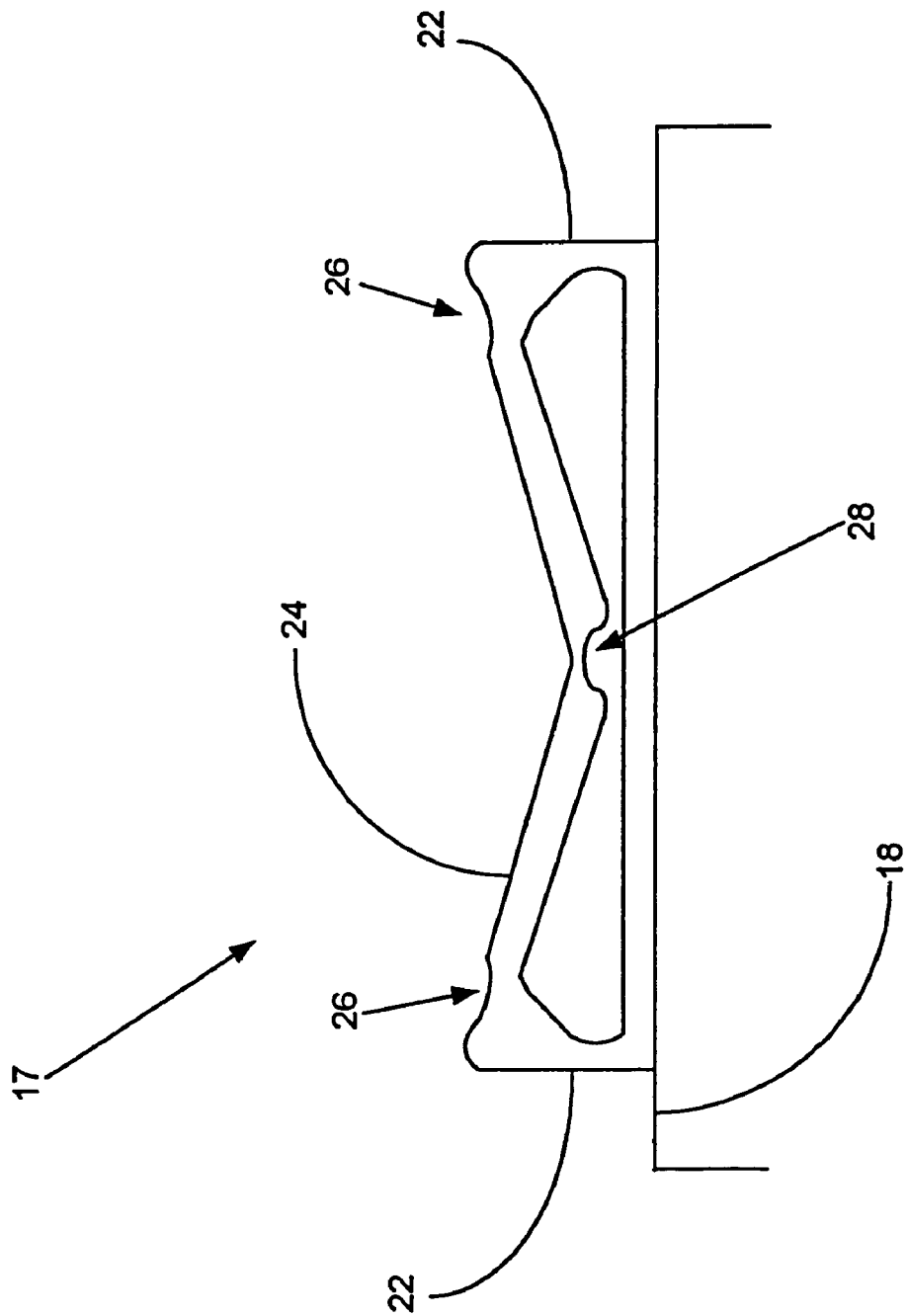
FIG. 6 is an enlarged view of an exemplary lock-out member of the reagent container of FIG. 1 in an used condition.

In another exemplary embodiment of the present invention, lock-out member 17 is envisioned by the present invention to be of a "two-position-snap" design in which a selectively weakened bridge member 24 integral with reagent container 10 is snap-displaced or toggled from an original "new" position to a "used" position. In such an embodiment, bridge member 24 is retained on container 10 as a permanent but displaced portion of the reagent container 10. FIG. 4 illustrates lock-out member 17 as comprising a weakened bridge member 24 supported between two pylons 22 extending outwardly from edgewall 18. Importantly, bridge member 24 is caused to be weakened in its central region due to a notch 28 formed contiguous with open region 30 and bridge member 24 is caused to be weakened at both of its ends by narrowed cusps 26 where the bridge member 24 enjoins pylons 22. Cusps 26 are formed on the opposite side of bridge member 24 from notch 28 in order to facilitate a "collapsing" of bridge member 24 from its "original, unused" position to an inwardly displaced position indicative of a "previously used" condition, seen in FIG. 6 and as explained hereinafter. The degree of weakening of bridge member 24 separately and independently by cusps 26 and by notch 28 may be adjusted so that the displacement of bridge member 24 from the new, unused condition of FIG. 4 and the used condition of FIG. 6 is a permanent displacement. Consequently, bridge member 24 "toggles" from its unused condition of FIG. 4 to its used condition of FIG. 6. An open region 30 is also formed between bridge member 24, pylons 22 and edgewall 18 to further accommodate such toggling of bridge member 24. FIG. 5 is a perspective view of bridge member 24 in an original "new" position.

Figure 3:
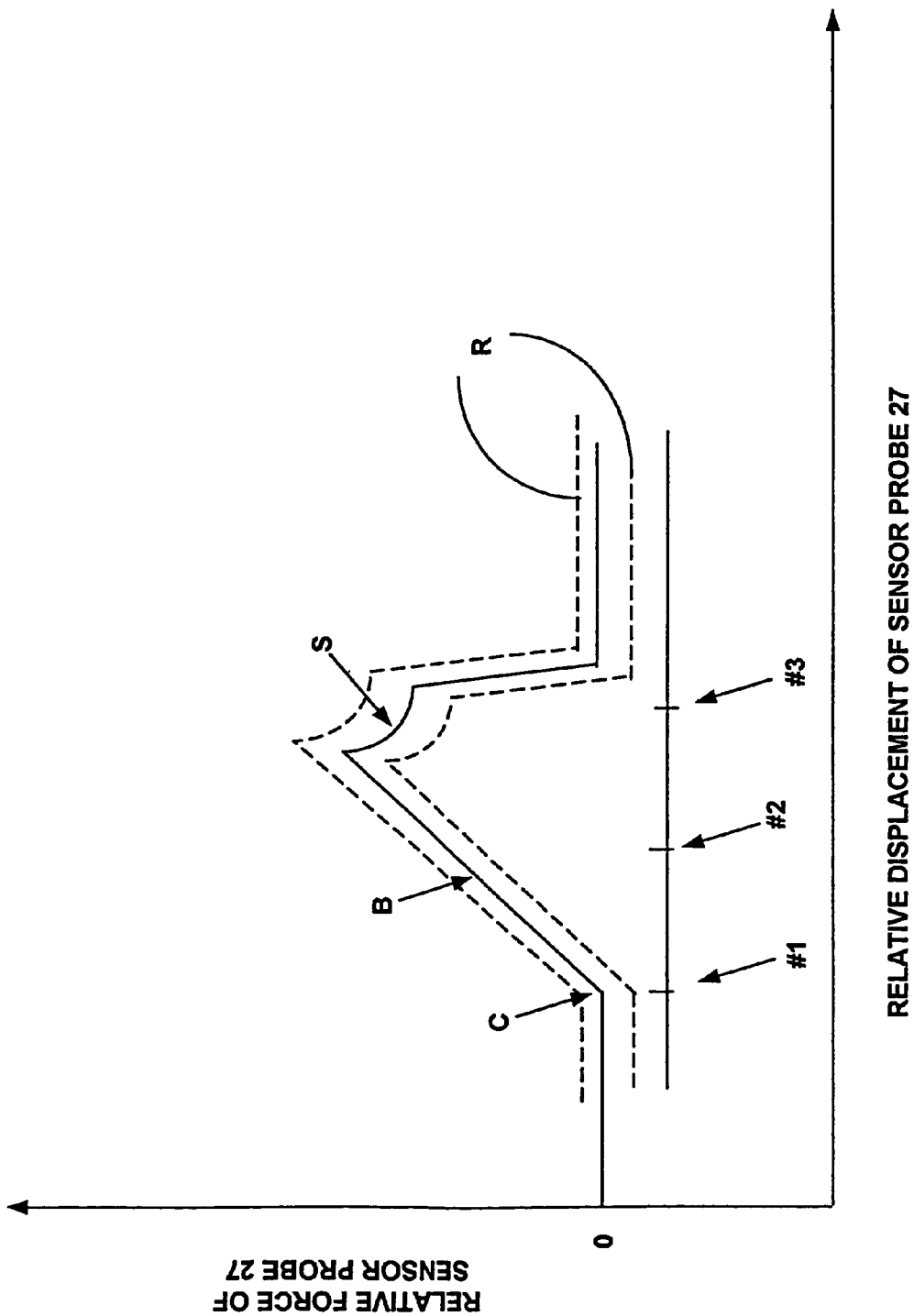
FIG. 3 illustrates signals typically generated by the sensor probe of FIG. 2A when practicing the present invention.

As explained later, in practicing the method of the present invention, in the embodiment illustrated by FIGS. 4 and 5, during the installation of a "new, unused" container 10 onto an analyzer, container 10 is automatically urged by a motorized transducer against a displacement probe and bridge member 24 is caused to be permanently displaced into a "collapsed" position as seen in FIG. 6. The method by which bridge member 24 is displaced into a "collapsed" position may vary; generally however, either the position and/or displacing force of the probe and/or the displacement alone of a moveable probe may be monitored and are required to be within certain predetermined ranges. FIG. 3 discussed earlier is an example of monitoring the displacing force of a sensor as a function of relative displacement of the sensor in order to determine the used-condition or new-condition of any reagent container.

Figure 7:
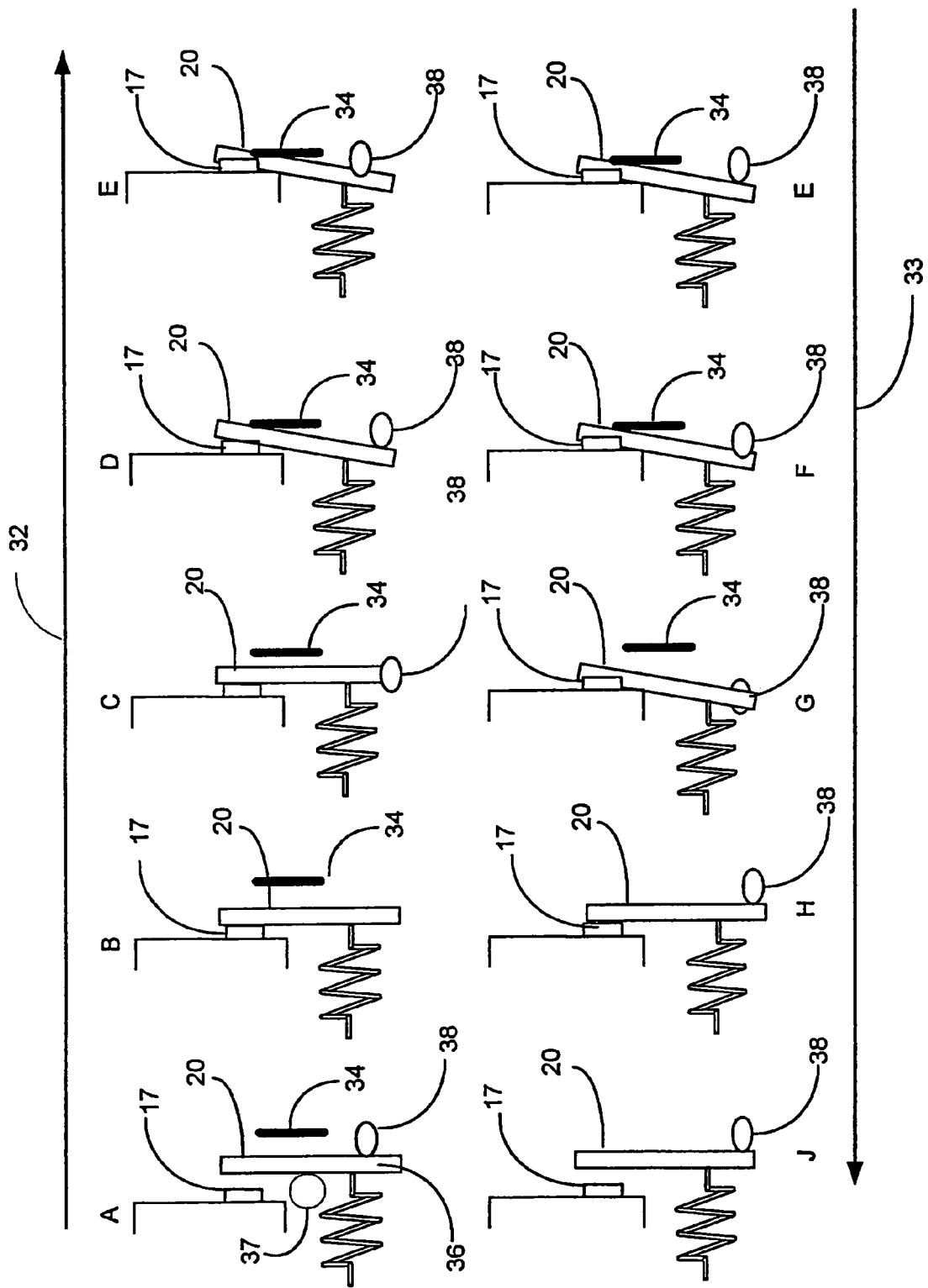
FIG. 7 is a schematic elevation view of the reagent container of FIG. 1 illustrating an exemplary embodiment of the present invention employing the lock-out member of FIG. 4.

In this alternate exemplary method of practicing the present invention, illustrated in FIG. 7 and using a container 10 having the lock-out member 17 of FIGS. 4-6, whenever a container 10 is initially inserted into an analyzer (stage A, upper portion of FIG. 7), the container is urged rightwards by a conventional transducer (not shown) so that lock-out member 17 is moved in the direction indicated by arrow 32 (left-to-right) into contact with a moveable sensor probe 20 (stage B). In this embodiment, the sensor probe has the form of a displacement probe 20 equipped with a conventional displacement sensor 38 and is biased against a stop 37 to a vertical orientation by a biasing spring 36. Container 10 is continued to move rightwards (stage C) as shown until probe 20 engages a stationary stop 34 (stage D) and is forced against lock-out member 17 proximate notch 28 (see stage D, FIG. 8). Container 10 is further continued to move rightwards by the transducer until stationary stop 34 (stage E) restricts further movement of displacement probe 20 which causes the weakened bridge member 24 of lock-out member 17 to snap into a collapsed state like that shown in FIG. 6. As described before, cusps 26 and notch 28 are provided to facilitate the collapsing of bridge member 24 to a permanent inwardly displaced position so that it becomes possible to ascertain that container 10 has been previously placed onto an analyzer and is therefore in a "previously used" condition.

Figure 9:
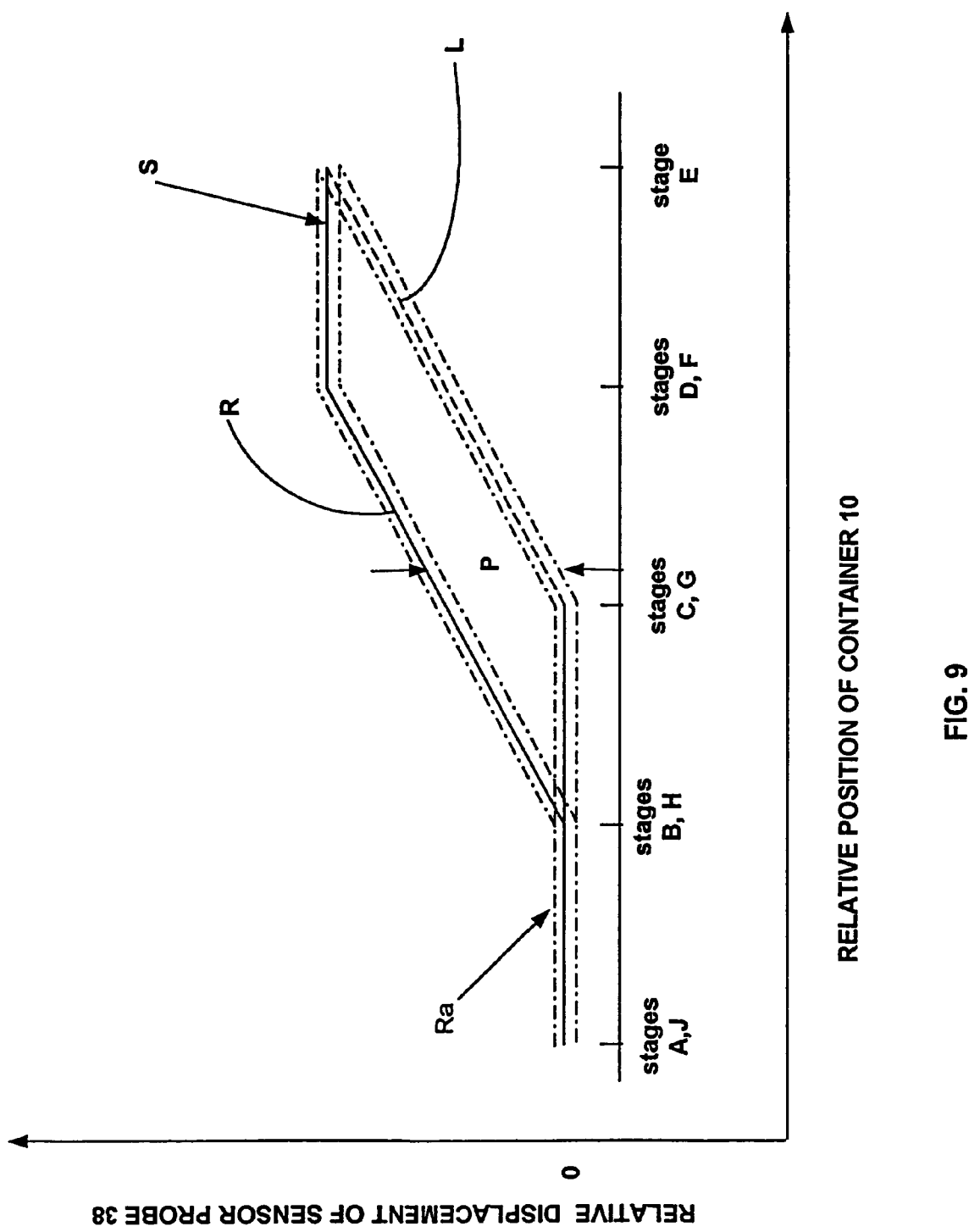

At this point, an analysis like that shown in FIG. 9 of the amount of displacement of displacement probe 20 relative to the length of travel of container 10 may be made to determine whether or not container 10 has been previously used. Such an analysis evaluates the displacement of probe 20 at stage C—if container 10 has been previously used, bridge member 24 will be in a collapsed state like that seen in FIG. 6 and probe 20 will be displaced a predetermined distance less than the length of travel of probe 20 if the bridge member 24 is in the un-collapsed state like that seen in FIG. 4, indicative of an unused container. Equivalently, if container 10 is previously used and bridge member 24 is in a collapsed state, then container 10 must be moved a greater distance rightwards to achieve the same displacement of probe 20 as if the bridge member 24 is in the un-collapsed state like that seen in FIG. 4, indicative of an unused container.

In practice, for an unused container 10 at stage B, container 10 has been moved into the analyzer a predetermined distance and is brought into contact with displacement probe 20. As soon as any movement of container 10 rightwards beyond stage B occurs, like shown at stage C, sensor 38 of displacement probe 20 must begin to send a signal indicative of movement elsewise container 10 may be determined to have been previously used and the analyzer may be optionally programmed to reject such a used container 10. The purpose of continuing movement of container 10 beyond stage B is to cause bridge member 28 to toggle into the "used" position shown in FIG. 6 whenever such a container 10 is initially placed onto an analyzer. It is desirable to also make a complete analysis of the condition of container 10 in order to detect any unwarranted attempts to over-ride the effectiveness of lock-out member 17, for instance using tape to patch over the collapsed bridge member 24 of a previously used container 10.

The lowermost portion of FIG. 7 shows the opposite interactions occurring as container 10 is moved leftwards (right-to-left) as indicated by arrow 33 into an operating position within the analyzer after it has been determined whether container 10 is new and unused or previously used by employing the present invention. Stage E is repeated for the sake of illustration only. At stage F, container 10 has been moved to a location equivalent to stage D sufficient for probe 20 to begin to break free of stationary stop 34. Leftwards movement of container 10 continues, stages G-H-J until container 10 is away from stop 34 and probe 20 is held in its original vertical orientation by biasing spring 36.

Figure 8:
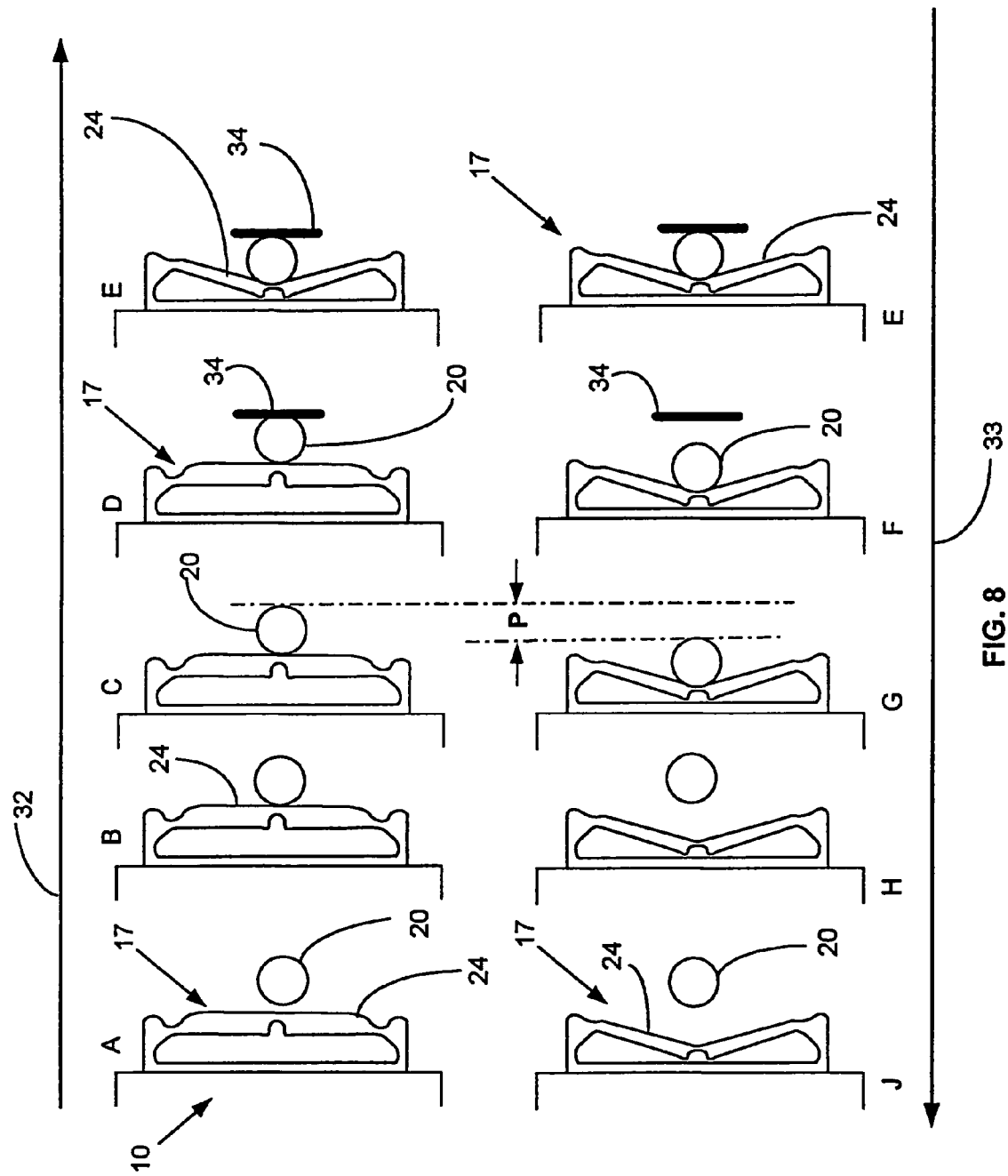
FIG. 8 is a schematic plan view illustrating the embodiment of FIG. 7 employing the lock-out member of FIG. 4; and, FIG. 9 is a plot of sensor signals generated when practicing the embodiment of FIG. 7.

FIG. 8 is a schematic plan view corresponding to the stages A-J in FIG. 7 (stage "I" is not used) and is presented for further clarity in explaining this embodiment of the present invention. Weakened bridge member 24 may be seen initially contacting probe 20 at stage B, continuing rightwards motion at stage C and probe 20 being moved against stationary stop 34 at stage D. Arrows 32 and 33 again indicate right-to-left and left-to-right motion, respectively, only for purposes of illustration and explanation. Obviously all that is required to practice the present inventive method is relative movement of the container 10. Weakened bridge member 24 is illustrated in stage E as collapsed from a unused condition to a used condition by continued movement of container 10 further forcing lock-out member 17 against stop 34. As the container 10 is moved leftwards into an operating position within the analyzer, beginning with stage F in the lower portion of FIG. 8, the biasing action of spring 36 causes displacement probe 20 to be pulled against the now collapsed bridge member 24. Consequently, bridge member 24 will be in different displacements, indicated by the dot-dashed vertical lines in FIG. 8, in stages G and C if, and only if, a legitimate collapsing action has occurred to weakened bridge member 24. A similar different displacements exists at stages D and F. That is, when container 10 is in the same location at stages C and G, or D and F, displacement probe 20 will have a predetermined difference in vertical orientation, as denoted by the letter "P".

FIG. 9 illustrates signals like those generate by sensor 38 in practicing this embodiment of the present invention. Solid line "R" indicates signals received by sensor 38 during relative rightwards movement of container 10 and the dashed line "L" indicates signals received by sensor 38 during relative leftwards movement of container 10. Initial contact between lock-out member 17 and probe 20 takes place at stage B in FIGS. 8 and 9; with continued rightwards movement of container 10, probe 20 is displaced rightwards, stage C of FIGS. 8 and 9, and sensor probe 38 generates an increasing displacement signal like that shown at stages C and D in FIGS. 8 and 9. Continued movement of container 10, stage D, by a shuttle mechanism (not shown) rightwards causes probe 20 to snap or toggle weakened bridge member 28 from its original new condition to a used condition, stage E of FIG. 8, and as indicated by the letter "S" prior to stage E in FIG. 9. As described previously, a key feature of the present invention is that whenever a container 10 is initially placed onto an analyzer, if sensor 38 output signals, indicative of the displacement of probe 20 as a function of the position of container 10, do not fall within previously predetermined ranges, for example within a range of about 15% to 20% of the relative displacement signal values indicated in FIG. 9, it may be automatically determined whether a reagent container is new and unused or whether the reagent container has been previously used. Such a range is illustrated in FIG. 9 by dot-dashed lines Ra. As a fail-safe, confirming mechanism, the displacement signal of sensor 38 generated at container locations corresponding to stages C and G, or D and F, displacement probe 20 will have a predetermined difference displacement as measured by sensor 38, again shown by the letter "P" in FIG. 9, at stages C and G.

In practicing either embodiment of the present invention, the analyzer may be programmed to automatically eject a previously used reagent container, shut-down or the analyzer may allow sample analysis to continue uninterrupted with reagents from a previously used container but automatically noting such re-use in the reported analytical results. The degree of skill required to cause an analyzer to automatically perform such actions is well within the range of routine computer programs.

Accommodating a myriad of different potential designs for lock-out member 17 within a container is a task regularly encountered within the art and need not be described herein. It is sufficient that the inventive teaching presented herein that a reagent container may be determined to have previously been used by examining a physical feature of the container when it is initially placed into an analyzer in order to ascertain the position of a lock-out member, need only be presented to artisans for equivalent variations to be rendered obvious. It is therefore to be understood that the embodiments of the invention disclosed herein are illustrative of the principles of the invention and that other modifications may be employed which are still within the scope of the invention. For instance, flag member 21 may be of a variety of physical shapes, lock-out member 17 may be placed at a variety of locations on container 10, bridge member 24 may be caused to snap fully apart when in a collapsed stage, etc. For these reasons, the present invention is not limited to those embodiments precisely shown and described in the specification but only by the following claims.

We claim:

1. A multi-compartment reagent container in the form of a container strip generally tapered in a substantially elongated wedge-like manner from a first edgewall to a second edgewall between first and second sidewalls, the container having a flag member comprising a weakened bridge that is displaceable from a first position to a second position and is attached to an edgewall wherein the weakened bridge is mounted between first and second pylons attached to an edgewall, the first pylon attached to the edgewall proximate the intersection of the edgewall and the first sidewall and the second pylon attached to the edgewall proximate the intersection of the edgewall and the second sidewall.

2. The container of claim 1 wherein the bridge and the pylons define an open region proximate said at least one edgewall.

3. The container of claim 2 wherein the weakened bridge comprises a notch formed near the middle of the bridge contiguous with the open region.

4. The container of claim 3 wherein the weakened bridge further comprises a pair of cusps formed at the ends of the bridge enjoining the pylons.

5. The container of claim 4 wherein the cusps are formed on the opposite side of the bridge from said notch.

6. A reagent container comprising:
a plurality of wells linearly arrayed, each well adapted to hold clinical reagent;
first and second opposed sidewalls enclosing said array of wells;
first and second edgewalls extending between and joining the first and second opposed sidewalls at first and second pairs of intersecting edgewalls and sidewalls, the edgewalls and sidewalls forming a generally tapered, wedge-like shaped container;
a first pylon attached directly to the first edgewall and extending outwardly therefrom;
a second pylon spaced apart from the first pylon and attached directly to the first edgewall and extending outwardly therefrom; and,
a bridge mounted between said first and second pylons said bridge being displaceable from a first position to a second position whenever the container is initially placed onto an analyzer.

7. The reagent container of claim 6 wherein the first pylon is attached proximate the first pair of intersecting edgewalls and sidewalls and wherein the second pylon is attached proximate the second pair of intersecting edgewalls and sidewalls.

8. The reagent container of claim 6 wherein said wells are closed and sealable on a top surface.

9. The reagent container of claim 6 wherein said first edgewall is wider than the second edgewall.

10. The reagent container of claim 6 wherein said wells contain clinical reagents.

11. The reagent container of claim 6 wherein the bridge has a notch formed near the middle thereof.

12. The reagent container of claim 11 wherein the bridge further comprises a pair of cusps formed at the ends of the bridge enjoining the pylons.

13. The reagent container of claim 12 wherein the cusps are formed on the opposite side of the bridge from said notch.

14. The reagent container of claim 13 wherein the bridge and the pylons define an open region proximate said first edgewall.

15. A reagent container comprising:
a linear array of wells adapted to hold clinical reagents;
first and second opposed sidewalls enclosing said array of wells;
first and second edgewalls extending between and joining the first and second opposed sidewalls, the edgewalls and sidewalls forming a generally tapered, wedge-like shaped container;
a pair of pylons attached directly to the first edgewall and extending outwardly therefrom;
a bridge that is displaceable from a first position to a second position mounted between said pair of pylons.

16. The reagent container of claim 15 wherein said wells are closed and sealable on a top surface.

17. The reagent container of claim 15 wherein said first edgewall is wider than the second edgewall.

18. The reagent container of claim 15 wherein said wells contain clinical reagents.

19. The reagent container of claim 15 wherein the bridge has a notch formed near the middle thereof 20. The reagent container of claim 19 wherein the bridge further comprises a pair of cusps formed at the ends of the bridge enjoining the pylons.

21. The reagent container of claim 20 wherein the cusps are formed on the opposite side of the bridge from said notch.

22. The container of claim 18 wherein the bridge and the pylons define an open region proximate said first edgewall.

* * * * *

UNITED STATES PATENT AND TRADEMARK OFFICE
CERTIFICATE OF CORRECTION

PATENT NO. : 7,661,551 B2 Page 1 of 1
APPLICATION NO. : 10/858156
DATED : February 16, 2010
INVENTOR(S) : Gebrian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 999 days.

Signed and Sealed this

Thirtieth Day of November, 2010

David J. Kappos
*Director of the United States Patent and Trademark Office*